United States Patent [19]

Colin et al.

[11] Patent Number: 4,924,012
[45] Date of Patent: May 8, 1990

[54] PROCESS FOR PREPARING DERIVATIVES OF BACCATINE III AND OF 10-DEACETYL BACCATINE III

[75] Inventors: Michel Colin, Thoiry; Daniel Guenard, Montrouge; Françoise Gueritte-Voegelein, Les Ulis; Pierre Potier, Paris, all of France

[73] Assignee: Rhone-Poulenc Sante, Antony, France

[21] Appl. No.: 331,758

[22] Filed: Apr. 3, 1989

[30] Foreign Application Priority Data

Apr. 6, 1988 [FR] France ................. 88 04513

[51] Int. Cl.$^5$ ........................... C07D 305/14
[52] U.S. Cl. ........................ 549/510; 549/511
[58] Field of Search ................ 549/510, 511

[56] References Cited

U.S. PATENT DOCUMENTS 4,814,470  3/1989  Colin et al. ............... 514/449
4,857,653  8/1989  Colin et al. ............... 549/510

FOREIGN PATENT DOCUMENTS 0253738  1/1988  European Pat. Off. .

OTHER PUBLICATIONS

Gueritte-Voegelein et al., J. Natural Products, 50(1), pp. 9-18, 1987.
Lataste et al., Proc. Nat'l. Acad. Sci. USA, 81, pp. 4090-4094, Jul. 1984.

*Primary Examiner*—Glennon H. Hollrah
*Assistant Examiner*—Ba K. Trinh
*Attorney, Agent, or Firm*—Stevens, Davis, Miller & Mosher

[57] ABSTRACT

Process for preparing derivatives of baccatine III and of 10-deacetylbaccatine III, of general formula (I), in which R is hydrogen or acetyl, by condensation of an acid of general formula (II) with a derivative of baccatine III or of 10-deacetylbaccatine III of general formula (III), $R_1$, $R_2$ and $R_3$ denoting hydroxy-protecting groups, followed by the replacement of the protecting groups by hydrogen.

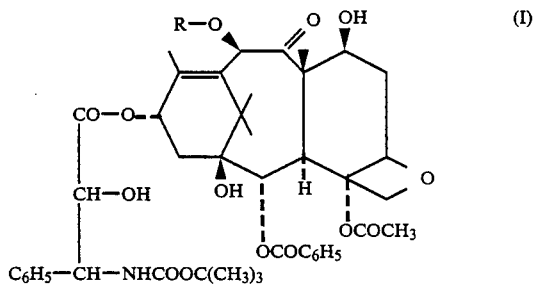

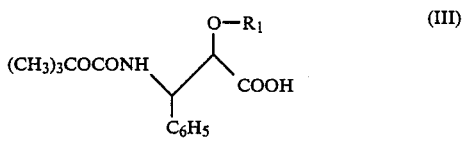

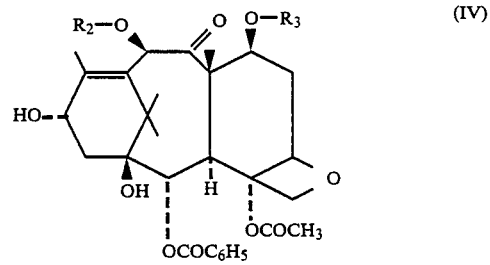

11 Claims, No Drawings

PROCESS FOR PREPARING DERIVATIVES OF BACCATINE III AND OF 10-DEACETYL BACCATINE III

The present invention relates to a process for preparing derivatives of baccatine III and of 10-deacetylbaccatine III, of general formula

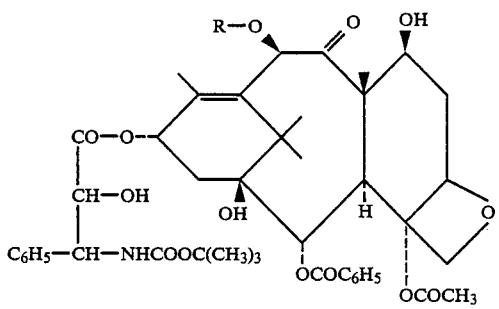

in which R denotes a hydrogen atom or an acetyl radical.

In European patent application EP No. 253,738, the products of general formula (I) and their preparation have been described. The products of general formula (I), especially the product of general formula (I) in which R denotes a hydrogen atom, exhibit especially advantageous antitumour and antileukaemic properties.

According to European patent application EP No. 253,738, the products of general formula (I) are obtained by the action of the sodium salt of tert-butyl N-chlorocarbamate on a product of general formula:

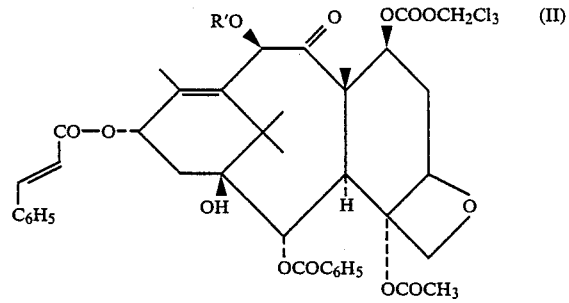

in which R' denotes an acetyl or 2,2,2-trichloroethoxycarbonyl radical, followed by the replacement of the 2,2,2-trichloroethoxycarbonyl group or groups by hydrogen. This process leads to a mixture of isomers which has to be separated and, as a result, not all the baccatine III or 10-deactylbaccatine III employed for the preparation of the product of general formula (II) can be converted to a product of general formula (I).

The present invention provides a process for preparing derivative of baccatine III or of 10-deacetylbaccatine III, of general formula

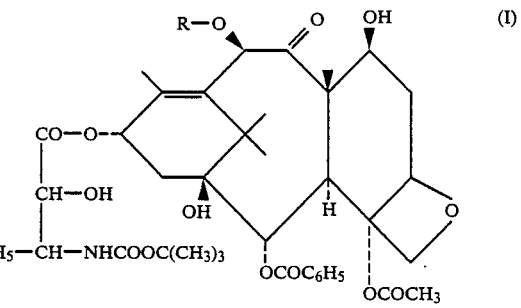

in which R denotes hydrogen or acetyl wherein an acid of general formula:

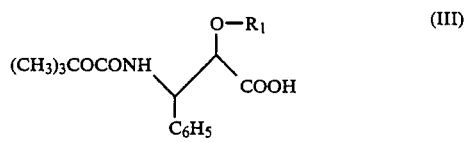

in which $R_1$ is a hydroxy-protecting group, is condensed with a taxan derivative of general formula:

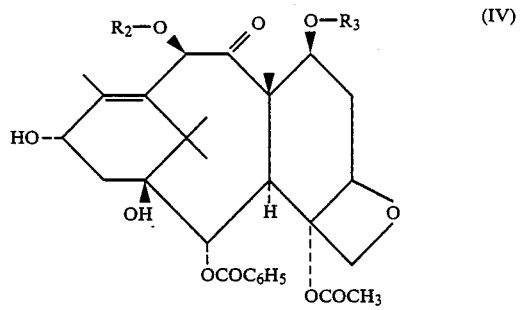

in which $R_2$ is an acetyl hydroxy-protecting group and $R_3$ is a hydroxy-protecting group, and the protecting groups $R_1$, $R_3$ and, where appropriate, $R_2$ are then replaced by hydrogen.

In the general formula (III), $R_1$ more especially denotes a methoxymethyl, 1-ethoxyethyl, benzyloxymethyl, ($\beta$-trimethylsilylethoxy)methyl, tetrahydropyranyl or 2,2,2-trichloroethoxycarbonyl group. Preferably, $R_1$ is a 1-ethoxyethyl group.

In the general formula (IV), the hydroxy-protecting groups defined by $R_2$ and $R_3$ are generally 2,2,2-trichloroethoxycarbonyl groups but it is also possible to use trialkylsilyl groups in which each alkyl portion contains 1 to 3 carbon atoms.

In general, the esterification of the taxan derivative of general formula (IV) with the acid of general formula (III) is performed in the presence of a condensing agent, e.g. a carbodiimide such as dicyclohexylcarbodiimide or a reactive carbonate such as di-2-pyridyl carbonate, and an activating agent, e.g. a dialkylaminopyridine such as 4-dimethylaminopyridine, working in an aromatic solvent such as benzene, toluene, a xylene, ethylbenzene, isopropylbenzene or chlorobenzene at a temperature of between 60° and 90° C.

It is especially advantageous to use a molar excess of acid of general formula (II) relative to the taxan derivative of general formula (IV), the condensing agent being used in a stoichiometric amount relative to the acid of general formula (III) and the activating agent e.g. 4-dimethylaminopyridine being used in a stoichiometric amount relative to the taxan derivative of general formula (IV). In general, at least 4 moles of acid of general formula (III) are used per mole of taxan derivative of general formula (IV).

The removal of the protecting groups from the ester obtained, of general formula:

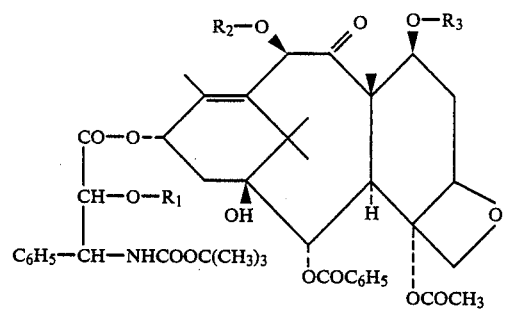

may be accomplished by means of zinc in the presence of acetic acid at a temperature of between 30° and 60° C., or by treatment by means of an inorganic or organic acid such as hydrochloric acid or acetic acid dissolved in an aliphatic alcohol containing 1 to 3 carbon atoms in the presence of zinc.

The acid of general formula (III) may be obtained by the saponification of an ester of general formula:

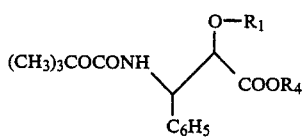

in which $R_1$ is defined as above and $R_4$ denotes alkyl containing 1 to 4 carbon atoms, and preferably ethyl, by means of an inorganic base such as an alkali metal hydroxide (lithium hydroxide, sodium hydroxide) or an alkali metal carbonate or bicarbonate (sodium bicarbonate, potassium carbonate), in an aqueous-alcoholic medium such as a methanol/water mixture, working at a temperature of between 10° and 40° C. and preferably in the region of 25° C.

The product of general formula (VI) may be obtained under the usual conditions for preparation of ethers, and more especially according to the processes described by J. N. Denis et al., J. Org. Chem., 51, 46–50 (1986), from the product of general formula:

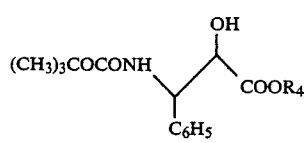

in which $R_4$ is defined as above.

The product of general formula (VII) may be obtained by the action of di-tert-butyl dicarbonate on a product of general formula:

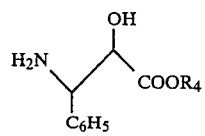

in which $R_4$ is defined as above. In general, the reaction is performed in an organic solvent such as methylene chloride, in the presence of a base such as sodium bicarbonate.

The product of general formula (VIII) may be obtained by the reduction of an azide of general formula:

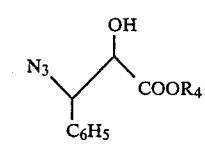

in which $R_4$ is defined as above, which is obtained according to the known methods for opening an epoxide of general formula:

in which $R_4$ is defined as above, by means of sodium azide in ethanol in the heated state.

The epoxide of general formula (X) may be obtained under the conditions described by F. W. Bachelor and R. K. Bansal, J. Org. Chem., 34, 3600–04 (1969).

For carrying out the process according to the invention, it is especially advantageous to use the products of general formulae (VI) to (X) in which $R_4$ denotes an ethyl radical.

When a product of general formula (X) is used in which $R_4$ denotes a radical other than ethyl, e.g. a tert-butyl radical, it is necessary, after opening the epoxide of general formula (X), to perform a transesterification reaction to convert the radical $R_4$ to an ethyl radical.

The taxan derivative of general formula (IV) in which $R_2$ denotes an acetyl or 2,2,2-trichloroethyl radical may be obtained by the action of 2,2,2-trichloroethyl chloroformate on baccatine III or 10-deacetylbaccatine III, working in a basic organic solvent such as pyridine, at a temperature of between 0° and 50° C.

The taxan derivative of general formula (IV) in which $R_2$ denotes an acetyl radical and $R_3$ denotes a trialkylsilyl radical may be obtained by the action of a halotrialkylsilane on baccatine III or 10-deacetylbaccatine III, followed, in the latter case, by the acetylation of the intermediate 7-trialkylsilyl-10-deacetylbaccatine III obtained.

In general, the reaction of the halotrialkylsilane with baccatine III or 10-deacetylbaccatine III is performed at a temperature in the region of 20° C., working in a basic organic solvent such as pyridine or in an inert organic solvent such as chloroform or dichloromethane in the presence of a tertiary amine such as triethylamine, pyridine or Hünig's base.

The acetylation of the 7-trialkylsilyl-10-deacetylbaccatine III is generally performed by means of acetyl chloride, working at a temperature in the region of 0° C. in a basic organic solvent such as pyridine or in an inert organic solvent such as chloroform, methylene chloride or dichloroethane in the presence of a tertiary amine such as pyridine or Hünig's base.

The example which follows, given without implied limitation, shows how the invention can be put into practice.

EXAMPLE threo-2-(1-Ethoxyethoxy)-3-tert-butyloxycarbonylamino-3-phenylpropionic acid (7.9 g; 22.4 mmol), anhydrous toluene (150 cc) and dicyclohexylcarbodiimide (4.6 g; 22.4 mmol), product of general formula (IV) in which $R_2$ and $R_3$ each denote a 2,2,2-trichloroethoxycarbonyl radical (5 g; 5.6 mmol) and 4-dimethylaminopyridine (0.68 g; 5.6 mmol) are introduced under an argon atmosphere into a 500-cc three-necked round-bottomed flask equipped with a stirrer and a thermometer. The mixture is heated for 7 hours at 70° C. under an argon atmosphere. After the mixture is cooled to 20° C., the precipitate formed is separated by filtration and then washed with cold toluene (50 cc).

The filtrate is concentrated to dryness and then taken up with methylene chloride (150 cc). The methylene chloride solution is washed with water (2×50 cc). The organic phase is concentrated to dryness.

A product (13.5 g) is thereby obtained, and this is chromatographed on Géduran silica (270 g), eluting with a methylene chloride/methanol (98:2 by volume) mixture. The impurities are removed by eluting with the mixture (1 liter) and then, by eluting again with the mixture (1 liter), the ester of general formula (V) in which $R_1$ denotes a (1-ethoxyethyl) radical and $R_2$ and $R_3$ each denote a 2,2,2-trichloroethoxycarbonyl radical (8 g) is obtained. By continuing the elution with the same mixture (1 liter), the starting taxan derivative (3.2 g) is recovered, and can be recrystallized in toluene.

The ester obtained above (8 g) is dissolved in an acetic acid/methanol (1:1 by volume) mixture (200 cc), and freshly reactivated powdered zinc (8 g) is then added. After 1 hour at 60° C. under an argon atmosphere, the reaction mixture is cooled to 20° C. and then filtered. The solid product is rinsed with the acetic acid/methanol mixture (50 cc). The combined filtrates are concentrated to dryness and the residue is then taken up with ethyl acetate. Some insoluble material is separated by filtration and washed 3 times with ethyl acetate (60 cc in total).

The combined organic phases are washed with half-saturated sodium bicarbonate solution (100 cc) and then with water (50 cc). The organic phases are dried over sodium sulphate. After filtration and evaporation of the solvent, a residue (5.5 g) is obtained, and this is chromatographed on Géduran silica (162 g), eluting with a hexane/ethyl acetate (1:1 by volume) mixture. Impurities (2.4 g) are separated off, followed by the (2'R, 3'S) oxy-amino derivative (0.595 g) and then the (2'R, 3'S) product of formula (I) in which R denotes a hydrogen atom (1.794 g), the purity of which is 90%.

The product is identical to that described in Example 3 of European patent application EP No. 253,738.

threo-2-(1-Ethoxyethoxy)-3-tert-butoxycarbonylamino-3-phenylpropionic acid may be prepared in the following manner:

Ethyl threo-2-(1-ethoxyethoxy)-3-tert-butoxycarbonylamino-3-phenylpropionate (10 g) is dissolved in ethanol (500 cc). Lithium hydroxide. $1H_2O$ (3.3 g), dissolved in water (250 cc) is added. The cloudy solution is stirred for 15 hours at a temperature in the region of 20° C. The ethanol is evaporated off under reduced pressure. Water (250 cc) is added, and the aqueous phase is then washed with methylene chloride (250 cc in total). The aqueous phase is acidified by adding 1 N hydrochloric acid to pH 3, extracting with methylene chloride (750 cc in total) as the acidification proceeds. After drying and concentration to dryness, threo-2-(1-ethoxyethoxy)-3-tert-butoxycarbonylamino-3-phenylpropionic acid (8.8 g) is obtained in a 95% yield and, after recrystallization in ethyl acetate, this has the following characteristics:

m.p. 152°–154° C.

infrared spectrum (in solution in chloroform): 3450, 2990, 2940, 1760 and 1735 cm$^{-1}$.

Ethyl threo-2-(1-ethoxyethoxy)-3-tert-butoxycarbonylamino-3-phenylpropionate may be prepared in the following manner:

Ethyl threo-2-hydroxy-3-tert-butoxycarbonylamino-3-phenylpropionate (30 g), dissolved in methylene chloride (1000 cc), pyridinium p-toluenesulphonate (2.4 g) and vinyl ethyl ether (93 cc) are introduced under an argon atmosphere into a 2-liter round-bottomed flask equipped with a stirrer and a thermometer. After 6 hours at a temperature in the region of 20° C., a few drops of pyridine are added so as to bring the pH to 7. The organic solution is washed with water (200 cc) half-saturated with sodium chloride, and then dried over magnesium sulphate. After filtration and removal of the solvents under reduced pressure, ethyl threo-2-(1-ethoxyethoxy) -3-tert-butoxycarbonylamino-3-phenylpropionate (38.6 g) is obtained in a yield in the region of 100%, its structure being confirmed by the proton nuclear magnetic resonance spectrum and by the mass spectrum.

Ethyl threo-2-hydroxy-3-tert-butoxycarbonylamino-3-phenylpropionate may be prepared in the following manner:

Ethyl threo-2-hydroxy-3-amino-3-phenylpropionate (136 g), dissolved in methylene chloride (1500 cc) is introduced into a 4-liter three-necked round-bottomed flask equipped with a stirrer, a thermometer and a condenser, and di-tert-butyl dicarbonate (196 g), dissolved in methylene chloride (500 cc), is then introduced slowly. There is an evolution of carbon dioxide and a temperature rise. After 20 minutes' reaction, sodium bicarbonate (50 g) is added and the temperature is allowed to fall to a value in the region of 20° C. in the course of 3 hours while the mixture is stirred. After filtration, the organic phase is washed twice with water and then dried over magnesium sulphate. After filtration and evaporation of the solvents, an oil which solidifies (305 g) is obtained. The solid is taken up with hexane (3500 cc). After 15 hours at a temperature of 4° C., the crystals obtained are separated by filtration and washed with hexane. Ethyl threo-2-hydroxy-3-tert-butoxycarbonylamino-3-phenylpropionate (148 g) is thereby obtained in a 73% yield, its structure being confirmed by the proton nuclear magnetic resonance spectrum and by the mass spectrum.

Ethyl threo-2-hydroxy-3-amino-3-phenylpropionate may be prepared in the following manner:

Ethyl threo-2-hydroxy-3-azido-3-phenylpropionate (178 g), dissolved in ethanol (2 at 95° C., is introduced into a 4-liter three-necked round-bottomed flask, and palladium on charcoal containing 10% (w/w) of palladium (20 g) is then added. After a purge with argon, a stream of hydrogen is passed through at a flow rate which is adjusted so as to maintain the temperature at below 30° C. After 1 hour, the flask is purged with argon. The reaction mixture is filtered on celite and then rinsed with ethanol. After concentration to dryness, an oil is obtained, which crystallizes to give, in a 92% yield, ethyl threo-2-hydroxy-3-amino-3-phenylpropionate (146 g), the structure of which is confirmed by the proton nuclear magnetic resonance spectrum and the mass spectrum.

Ethyl threo-2-hydroxy-3-azido-3-phenylpropionate may be prepared in the following manner:

tert-Butyl threo-2-hydroxy-3-azido-3-phenylpropionate (194 g) is dissolved in absolute ethanol (1 liter) in a 4-liter three-necked round-bottomed flask. A freshly prepared solution (550 cc) of hydrochloric acid in ethanol at a concentration of 13% by weight is added. After 3 hours at a temperature in the region of 20° C., the ethanol is evaporated off under reduced pressure. The residue is taken up with methylene chloride (1.5 liter) The methylene chloride solution is washed with saturated sodium bicarbonate solution (200 cc) and then with water. After drying and evaporation of the solvent, ethyl threo-2-hydroxy-3-azido-3-phenylpropionate (180 g) is obtained in a 99.7% yield, its structure being confirmed by the proton nuclear magnetic resonance spectrum and by the mass spectrum.

tert-Butyl threo-2-hydroxy-3-azido-3-phenylpropionate may be prepared in the following manner:

tert-Butyl 3-phenylglycidate (189 g), dissolved in ethanol (3 liters), is introduced into a 6-liter three-necked flask equipped with a stirrer, a thermometer and a condenser. Sodium azide (95 g) and ammonium chloride (75 g) are added and the mixture is then heated to 75° C. for 20 hours. Two-thirds of the ethanol are distilled off under reduced pressure at 50° C., water (4 liters) is then added and the evaporation of the ethanol is finally completed. After the aqueous suspension is cooled, a crystalline precipitate is obtained, which is separated by filtration and washed with water. After drying under reduced pressure in the presence of a phosphorus pentoxide, tert-butyl threo-2-hydroxy-3-azido-3-phenylpropionate (186.4 g) is obtained in an 82.4% yield, its structure being confirmed by the proton nuclear magnetic resonance spectrum and by the mass spectrum.

tert-Butyl 3-phenylglycidate may be prepared according to the process described by F. W. Bachelor and R. K. Bansal, J. Org. Chem., 34, 3600 (1969). The product obtained is purified by chromatography on Merck 7734 silica, so as to obtain tert-butyl cis-3-phenylglycidate (200 g).

The product of general formula (IV) in which $R_2$ and $R_3$ each denote a 2,2,2-trichloroethoxycarbonyl radical may be prepared according to the process described in European patent application EP No. 253,738.

We claim:

1. A process for preparing a derivative of baccatine III or of 10-deacetylbaccatine III, of general formula:

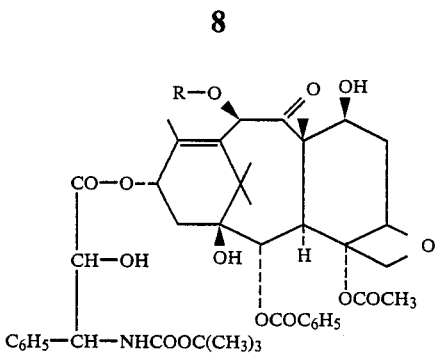

in which R denotes hydrogen or acetyl, wherein an acid of general formula:

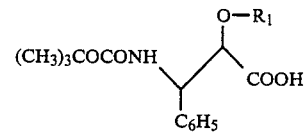

in which $R_1$ is a hydroxy-protecting group, is condensed with a taxan derivative of general formula

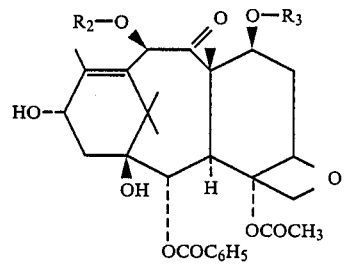

in which $R_2$ is an acetyl group or a hydroxy-protecting group and $R_3$ is a hydroxy-protecting group, and the protecting groups $R_1$, $R_3$ and, where appropriate, $R_2$ are then replaced by hydrogen.

2. A process according to claim 1, wherein $R_1$ is chosen from the group comprising methoxymethyl, 1-ethoxyethyl, benzyloxymethyl, (β-trimethylsilylethoxy)methyl, tetrahydropyranyl and 2,2,2-trichloroethoxycarbonyl.

3. A process according to claim 2, wherein $R_1$ is 1-ethoxyethyl.

4. A process according to claim 1, wherein the hydroxy-protecting groups $R_2$ and $R_3$ which may be the same or different are each chosen from 2,2,2-trichloroethoxycarbonyl or trialkylsilyl groups in which each alkyl portion contains 1 to 3 carbon atoms.

5. A process according to claim 4, wherein the hydroxy-protecting group is 2,2,2-trichloroethoxycarbonyl.

6. A process according to claim 1, wherein the condensation is performed in the presence of a condensing agent and an activating agent.

7. A process according to claim 6, wherein the condensing agent is chosen from carbodiimides and reactive carbonates and the activating agent is chosen from dialkylaminopyridines.

8. A process according to claim 7, wherein the condensing agent is chosen from dicyclohexylcarbodiimide and di-2-pyridyl carbonate, and the activating agent is 4-dimethylaminopyridine.

9. A process according to claim 1, wherein the condensation is preformed in an aromatic solvent chosen from benzene, toluene, xylenes, ethylbenzene, isopropylbenzene and chlorobenzene.

10. A process according to claim 1, wherein the condensation is performed at a temperature of between 60° and 90° C.

11. A process according to claim 1, for replacing by hydrogen of the protecting groups $R_1$, $R_3$ and, where appropriate, $R_2$ on the intermediate product of general formula:

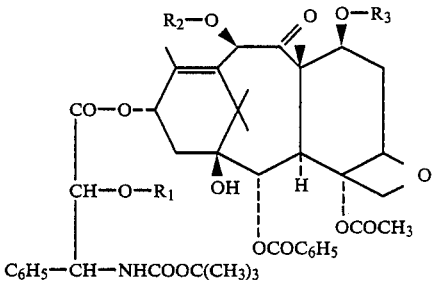

comprising treating said intermediate with zinc in the presence of acetic acid or with an inorganic or organic acid dissolved in an aliphatic alcohol containing 1 to 3 carbon atoms.

* * * * *